US010322051B2

(12) United States Patent
Arimura et al.

(10) Patent No.: US 10,322,051 B2
(45) Date of Patent: Jun. 18, 2019

(54) OPERATING TABLE

(71) Applicants: FUJIDENOLO CO., LTD., Aichi (JP); MEDIPOLIS MEDICAL RESEARCH INSTITUTE, Kagoshima (JP)

(72) Inventors: Takeshi Arimura, Kagoshima (JP); Mitsugi Matsuyama, Kagoshima (JP); Takashi Ogino, Kagoshima (JP); Yoshio Hishikawa, Kagoshima (JP); Hideki Miyazaki, Aichi (JP); Yoshitaka Taguchi, Aichi (JP); Keiichi Noma, Aichi (JP)

(73) Assignees: FUJIDENOLO CO., LTD, Aichi (JP); MEDIPOLIS MEDICAL RESEARCH INSTITUTE, Kagoshima (JP)

( * ) Notice: Subject to any disclaimer, the term of this patent is extended or adjusted under 35 U.S.C. 154(b) by 81 days.

(21) Appl. No.: 15/124,371

(22) PCT Filed: Mar. 10, 2015

(86) PCT No.: PCT/JP2015/056891
§ 371 (c)(1),
(2) Date: Sep. 8, 2016

(87) PCT Pub. No.: WO2015/137290
PCT Pub. Date: Sep. 17, 2015

(65) Prior Publication Data
US 2017/0020761 A1    Jan. 26, 2017

(30) Foreign Application Priority Data
Mar. 10, 2014   (JP) ................................ 2014-046982

(51) Int. Cl.
*A61G 13/12*    (2006.01)
*A61N 5/10*    (2006.01)
(Continued)

(52) U.S. Cl.
CPC ........... *A61G 13/1295* (2013.01); *A61N 5/10* (2013.01); *A61B 6/0407* (2013.01); *A61G 13/04* (2013.01);
(Continued)

(58) Field of Classification Search
CPC .... A61G 13/12; A61G 13/122; A61G 13/128; A61G 13/1285; A61G 13/1295;
(Continued)

(56) References Cited

U.S. PATENT DOCUMENTS 6,260,220 B1 * 7/2001 Lamb .................... A61G 13/02
5/601

FOREIGN PATENT DOCUMENTS

JP      H09168569 A    6/1997
JP      2001513365 A   9/2001
(Continued)

OTHER PUBLICATIONS

International Search Report issued in corresponding application No. PCT/JP2015/056891 dated May 12, 2015 (4 pages).

(Continued)

*Primary Examiner* — Fredrick C Conley
(74) *Attorney, Agent, or Firm* — Osha Liang LLP (57) ABSTRACT

An operating table includes a patient placement table for placing and securing a patient in a required posture; a main body for supporting the patient placement table; engaging pieces for removably coupling the patient placement table to the main body; and a motor for rotating the patient placement table with a head-feet direction of the patient as a rotation axis to hold the patient placement table at any given rotation angle.

5 Claims, 5 Drawing Sheets (51) Int. Cl.
　　　*A61B 6/04*　　　(2006.01)
　　　*A61G 13/04*　　　(2006.01)
(52) U.S. Cl.
　　　CPC .... *A61G 13/122* (2013.01); *A61N 2005/1087*
　　　　　　　　(2013.01); *A61N 2005/1097* (2013.01)
(58) Field of Classification Search
　　　CPC .... A61G 13/04; A61B 6/0407; A61B 6/0435;
　　　　　　　　A61B 6/0414; A61B 6/0421; A61N
　　　　　　　　　　　　　　　　　　　　2005/1097
　　　USPC ............................................ 5/601, 607, 621
　　　See application file for complete search history.

(56)　　　　　　　　References Cited

FOREIGN PATENT DOCUMENTS

| JP | 2002516719 A | 6/2002 |
|---|---|---|
| JP | 2013223722 A | 10/2013 |

OTHER PUBLICATIONS

Written Opinion of the International Searching Authority issued in corresponding application No. PCT/JP2015/056891 dated May 12, 2015 (5 pages).

\* cited by examiner

OPERATING TABLE

TECHNICAL FIELD

The present invention relates to an operating table configured to rotate a placed patient with a head-feet direction as a rotation axis and secure the patient at any given angle.

BACKGROUND ART

Recently, there has been progressed a development of a curative treatment for breast cancer by radiation of particle beam such as proton beam and heavy particle beam. It is preferable for this radiation therapy with proton beam to keep breasts to be treated away from a chest wall as much as possible to avoid a negative effect to a part other than the breasts due to the radiation with proton beam. To achieve this, it is required for the patient to be secured holding a state of drooping the breasts at an abdominal position. Meanwhile, for radiation with proton beam or heavy particle beam, the patient needs to be at a supine position. Therefore, for the radiation therapy with proton beam or heavy particle beam, an operating table configured to rotate the patient with a head-feet direction as a rotation axis is necessary.

As the operating table configured to secure and hold the patient in the rotated state, as disclosed in Patent Document 1, there has been known the following therapeutic bed. The therapeutic bed is constituted of a base frame and a platform that turns a patient around a rotation axis along a head-feet direction with respect to the base frame.

Patent Document 1: Japanese Unexamined Patent Application Publication No. 2002-516719

DISCLOSURE OF THE INVENTION

Problems to be Solved by the Invention

However, the conventional therapeutic bed disclosed in Patent Document 1 does not include a mechanism to secure a part of a body of the patient to the platform on which the patient is placed. This causes a failure that, it is difficult to perform the radiation therapy with proton beam without adversely affecting sites other than a lesion. Since the base frame and the platform are integrated, the conventional therapeutic bed has a large size. Accordingly, for examinations such as MRI and CT, it is necessary to take down the patient from the therapeutic bed and move and load the patient to another bed. This also causes a failure that data of the lesion site specified through the examinations is difficult to be used for the radiation therapy with proton beam.

An object of the present invention is to provide an operating table that solves the problems of the conventional therapeutic bed. The operating table eases the radiation therapy with proton beam without adversely affecting the sites other than the lesion. Additionally, information on the lesion site specified by a survey instrument is usable for the radiation with proton beam as it is. Thus, the operating table ensures effective treatment with proton beam.

Solutions to the Problems

In the present invention, the invention described in claim 1 is an operating table for holding a placed patient rotated about a head-feet direction as a rotation axis. The operating table includes a patient placement table, a main body, a coupling unit, and a rotation mechanism. The patient placement table places and secures the patient to hold the secured state of the patient also in a state where the patient is rotated such that breasts of the patient droop. The main body supports the patient placement table. The coupling unit removably couples the patient placement table to the main body with the patient placed. The rotation mechanism rotates the patient placement table about the rotation axis to hold the patient placement table at any given rotation angle. While the patient placement table is coupled to the main body using the coupling unit with the patient placed, the patient placement table rotates about the rotation axis by the rotation mechanism and is held at any given rotation angle.

The invention described in claim 2 according to the invention described in claim 1 is configured as follows. The patient placement table includes a mounting member for mounting a securing unit. The securing unit secures a chest of the secured patient.

The operating table according to the invention may include a movement and load assistance unit including a friction reduction member disposed on a contact surface of the patient placement table in contact with the main body and/or on a contact surface of the main body in contact with the patient placement table.

The invention described in claim 4 according to the invention described in claim 1 is configured as follows. The patient placement table includes strip-shaped side plates with wide width disposed upright near both right and left end edges of a rectangular bottom plate. The bottom plate and/or the side plates partially has a cutout.

The invention described in claim 5 according to the invention described in claim 1 is configured as follows. Even when the rotation mechanism rotates the patient placement table to have any posture, the coupling unit holds a joined part at which the placed patient table and the main body are joined together without separation, and a relative position between the placed patient table and the main body is held not to be displaced.

Effects of the Invention

With the operating table according to claim 1, while the body of the patient is secured (restrained) on the patient placement table in the required posture such as the supine position and the abdominal position, the patient placement table can be separated from the main body. For example, before the radiation therapy with proton beam, the patient placement table on which the patient whose body is secured is placed is conveyed with the stretcher or a similar member for predetermined examinations on the patient such as MRI and CT. After that, the patient placement table is further moved and loaded on the bed for treatment with proton beam with the stretcher or a similar member, thus the treatment with proton beam on the patient who keeps the identical posture becomes possible. Accordingly, with the operating table according to claim 1, the radiation therapy with proton beam can be effectively performed.

With the operating table according to claim 2, the patient placement table includes the mounting member to mount the securing unit that secures a part of the body of the secured patient. For example, for the radiation therapy with proton beam, the predetermined examinations and the radiation therapy with proton beam can be performed with the breasts of the patient separated from the chest wall and secured and held with the securing unit on the patient placement table. Accordingly, with the operating table according to claim 2, the radiation therapy with proton beam can be more effectively performed.

The operating table including the above-described movement and load assistance unit uses the movement and load assistance unit disposed at the main body. This allows the smooth separation of the patient placement table from the main body without applying a massive force. This also ensures moving and loading the patient placement table from a conveyance unit such as the stretcher to the main body.

The operating table according to claim 4 includes the cutouts at the patient placement table. The use of these cutouts ensures disposing the mounting members, which are to mount the securing unit to secure a part of the body, at positions appropriate for the patient and/or an affected part to be treated.

With the operating table according to claim 5, even if the patient placement table is rotated to be any posture, the operating table holds the joined part at which the patient placement table joins to the main body without separation. Additionally, a relative position between the patient placement table and the main body is held not to be displaced. Accordingly, the operating table can provide the patient placed on the patient placement table with a sense of security. Additionally, the operating table ensures the irradiation of proton beam on the lesion site at extremely good accuracy to treat the patient with proton beam or a similar beam.

DESCRIPTION OF PREFERRED EMBODIMENTS

<Structure of Operating Table>

The following describes an embodiment of an operating table according to the present invention in detail with reference to the drawings. FIG. 1 to FIG. 4 illustrate the operating table according to the present invention. An operating table 1 includes a patient placement table (patient placement securing means) 2, a main body 3, engaging pieces 4, 4, and so on, a drive control unit 5, and a similar member. The patient placement table 2 is to place and secure a patient P in a required posture. The main body 3 supports the patient placement table 2. The engaging pieces 4, 4, and so on function as coupling means that removably couple the patient placement table 2 to the main body 3. The drive control unit 5 controls a driving of a motor 14, which rotates the patient placement table 2, and a similar member. The patient placement table 2 and the main body 3 are separatable as necessary.

The main body 3 includes a base 6, which functions as a foundation, a front side annular portion 7, a rear side annular portion 8, a lower side beam 10, an upper side beam 9, and a similar member. The front side annular portion 7 and the rear side annular portion 8 incorporate a rotation mechanism to rotate the patient placement table 2. The lower side beam 10 and the upper side beam 9 place and hold the patient placement table 2.

The base 6 is made of a metal plate formed into a longitudinally-elongated flat rectangular parallelepiped shape whose side edge on one side is notched. The base 6 has casters 11, 11, and so on to move, at near four corners on the lower surface and securing means 12, 12, and so on to secure itself at a movement destination. The longitudinally-elongated rectangular-parallelepiped-shaped drive control unit 5 is installed on the rear surface of the base 6. This drive control unit 5 incorporates a controller (not illustrated) to control a rotation angle of the patient placement table 2, a controller (not illustrated) to control a height position when a pressing plate 17 is moved up and down, and a similar member.

Furthermore, the base 6 internally includes the motor 14 at the approximately center of the base 6. The motor 14 rotates the patient placement table 2 with a head-feet direction of the patient P as a rotation axis to secure the patient placement table 2 at any given rotation angle. Furthermore, the base 6 internally includes a long shaft 25 vertically across the front-to-rear. Gears 24a and 24b are fixedly secured to respective both ends on the front and the rear of this shaft 25. A gear (not illustrated) of a main shaft of the motor 14 meshes with a gear (not illustrated) at the center of the shaft 25. A rotation force of the motor 14 is transmitted to the front and the rear gears 24a and 24b via the shaft 25.

Both the front side annular portion 7 and the rear side annular portion 8 are formed by coating annular inner ring-shaped gears (not illustrated) and outer ring-shaped frames (not illustrated), which are relatively rotatable, with doughnut-shaped housings having hollows. The outer ring-shaped frame is fixedly secured to the base 6. At the inside near the lower ends of the front side annular portion 7 and the rear side annular portion 8, the inner ring-shaped gears each mesh with the gears 24a and 24b, which are disposed at both ends of the shaft 25.

Meanwhile, both the upper side beam 9 and the lower side beam 10 are formed into an I shape in plan view where both right and left side portions of longitudinally-elongated rectangle are largely notched. Outer surfaces of parts near front and rear end edges (wide width parts) are each fixedly secured to the inner ring-shaped gear, which is rotatably incorporated into the front side annular portion 7, and to the inner ring-shaped gear, which is rotatably incorporated into the rear side annular portion 8. The lower surface of the upper side beam 9 is disposed parallel to the top surface of the lower side beam 10 with a predetermined distance.

On the top surface of the lower side beam 10, ball bearings (movement and load assistance means) 26, 26, and so on are fitted to two parallel frames (not illustrated), which are disposed along a front-rear direction. The ball bearings 26, 26, and so on for smoothly moving and loading the patient onto the patient placement table 2 are rotatably disposed with a part of the upper portions projecting from the surface of the lower side beam 10. Furthermore, the quadrangular prism-shaped engaging pieces 4, 4, and so on are disposed near four corners on the top surface of the lower side beam 10 so as to be slidable to the inside and the outside by an air cylinder mechanism with the longitudinal direction matched with a width direction of the patient placement table 2. The engaging pieces 4, 4, and so on function as the coupling means to removably couple the patient placement table 2 to the main body 3.

Four long ball screws (coated with bellows pipes) 18, 18, and so on are mounted between the upper side beam 9 and the lower side beam 10 so as to couple the four corners of the upper side beam 9 and the lower side beam 10. These ball screws 18, 18, and so on that penetrate (are screwed with and penetrate) screw holes are drilled near four corners of the rectangular pressing plate 17, which is disposed in the middle of the upper side beam 9 and the lower side beam 10. Through the rotation of the ball screws 18, 18, and so on, the pressing plate 17 is vertically movable keeping a state parallel to the lower surface of the upper side beam 9 and the top surface of the lower side beam 10. The pressing plate 17 is formed into an approximately rectangular plate shape whose center parts at both right and left edges are notched. Elastic members 22 and 23 are mounted at the front and the rear of the lower surface of the pressing plate 17. A reinforcing frame 21 is mounted to the top surface of the pressing plate 17. A part of this reinforcing frame 21 droops from the right and left of the pressing plate 17.

Figure 1:
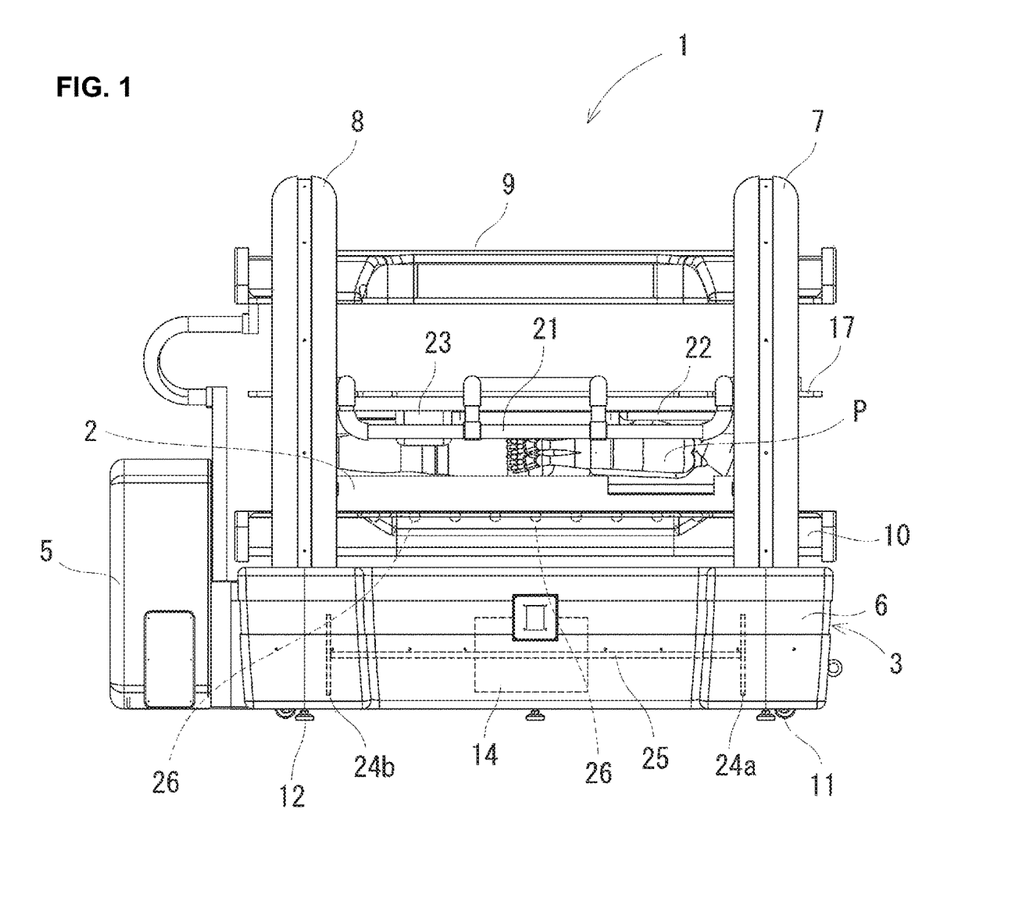
FIG. 1 is a front view of an operating table.
Figure 2:
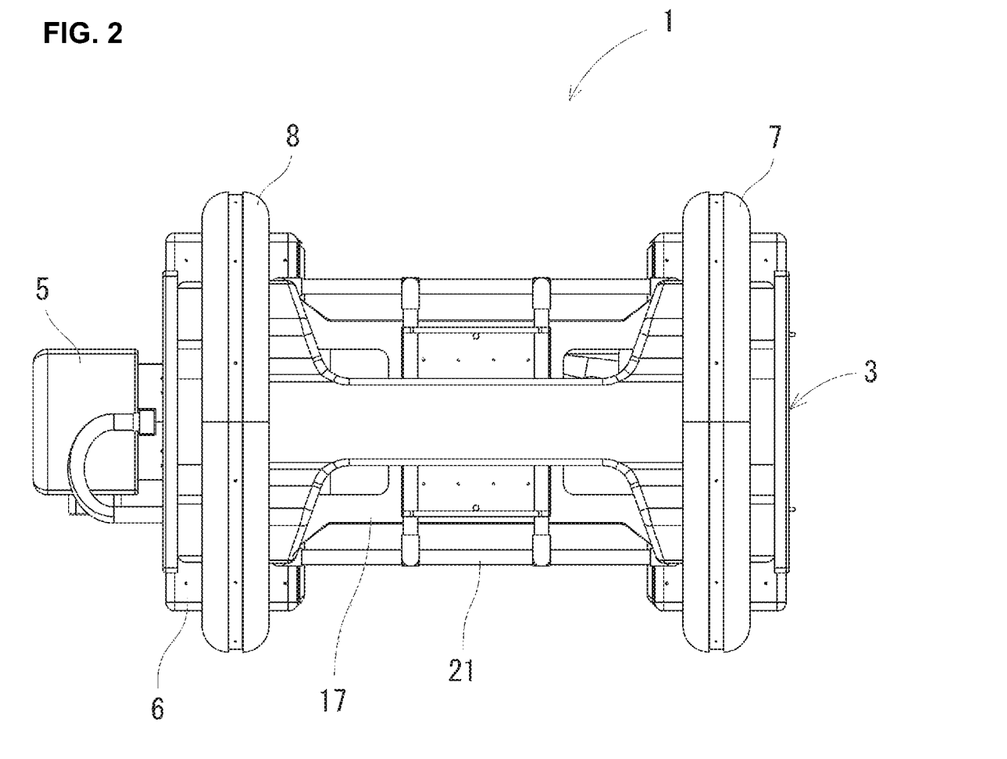
FIG. 2 is a plan view of the operating table.
Figure 3A:
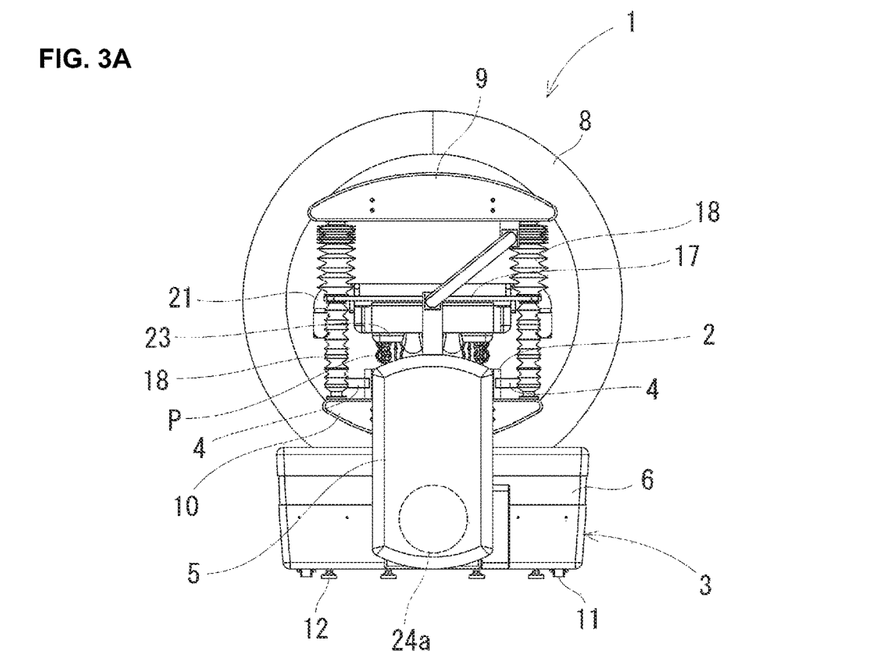
FIG. 3A is a left side view of the operating table.
Figure 3B:
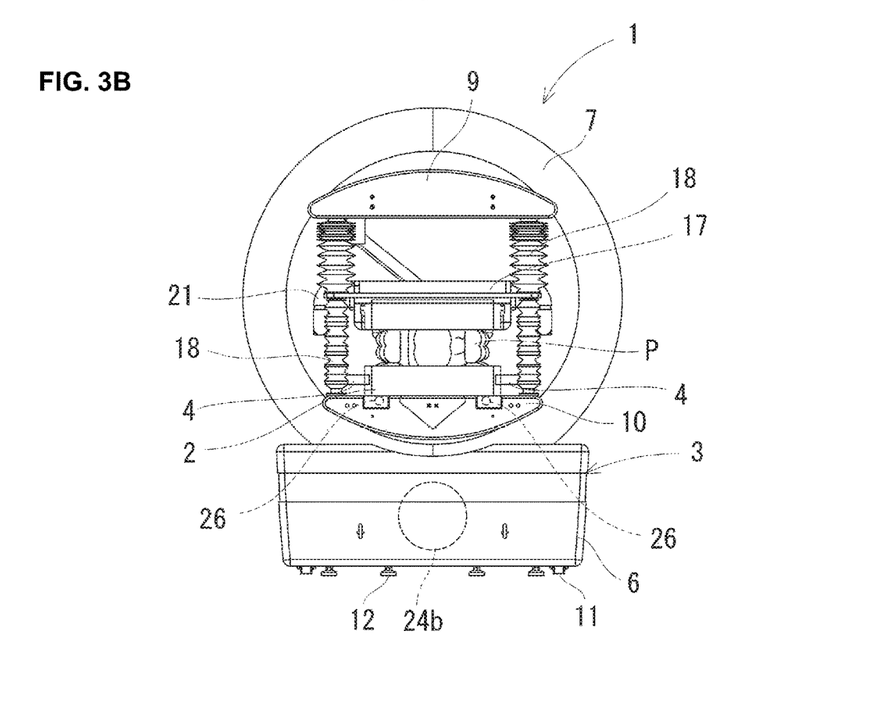
FIG. 3B is a right side view of the operating table.
Figure 4:
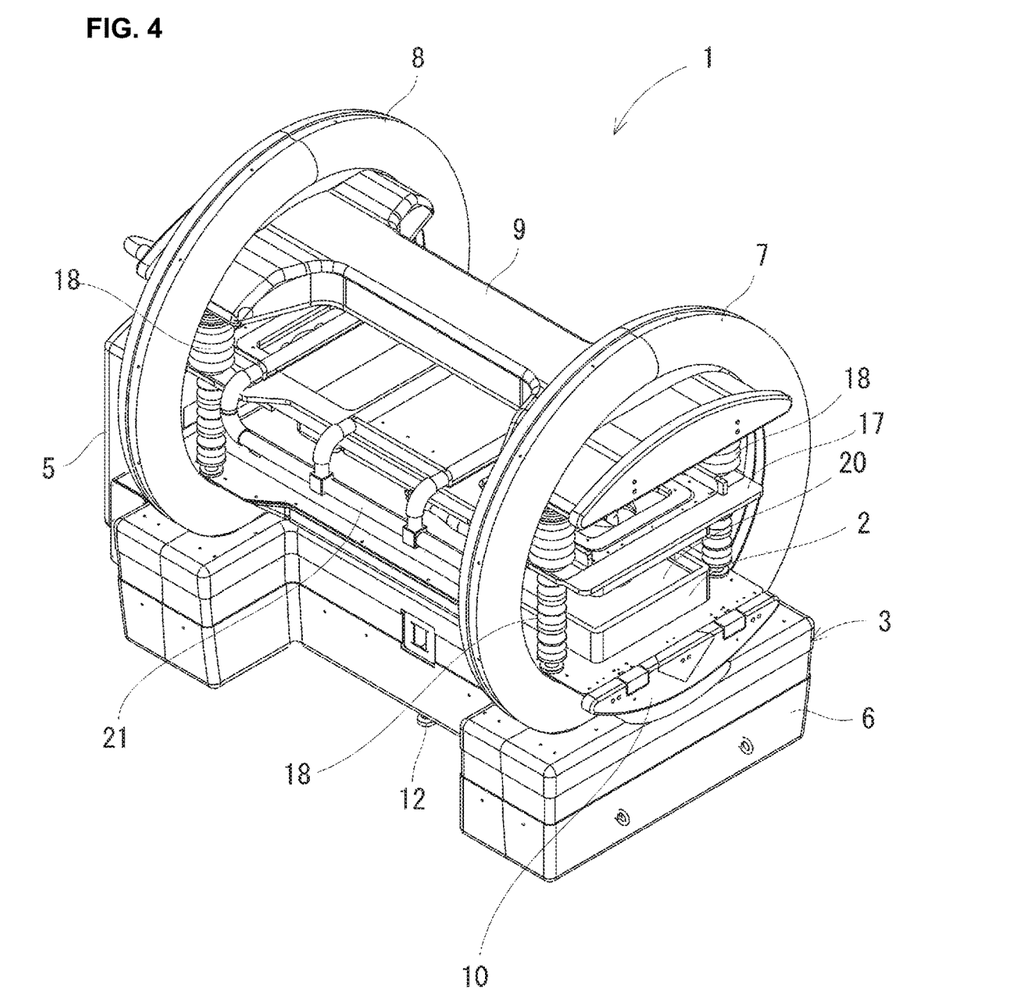
FIG. 4 is a perspective view of the operating table.
Figure 5A:
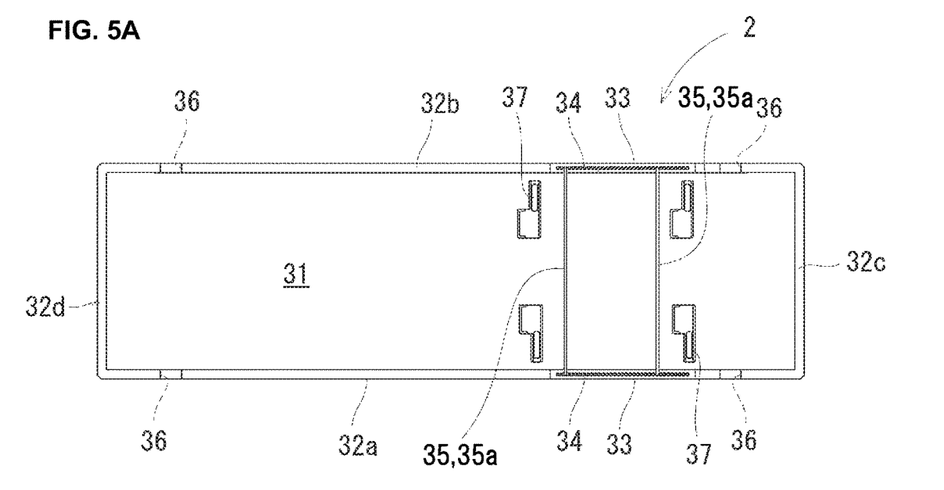
FIG. 5A is a plan view of a patient placement table separated from a main body.
Figure 5B:
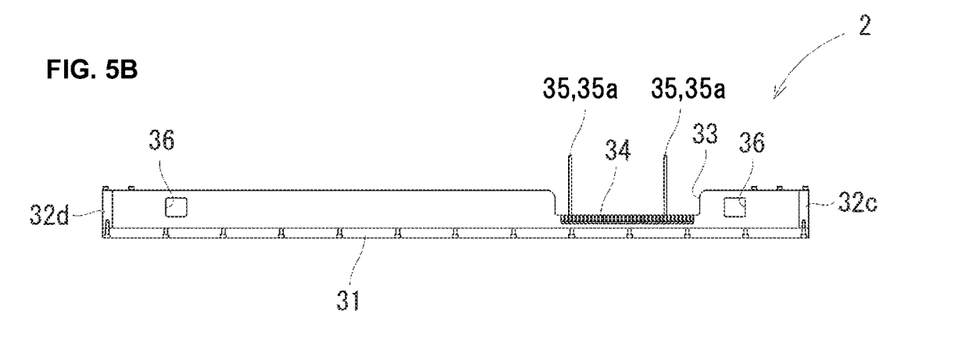
FIG. 5B is a front view of the patient placement table.
Figure 5C:
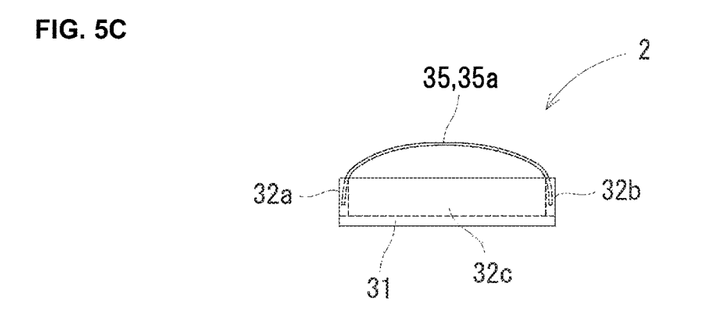
FIG. 5C is a right side view of the patient placement table.

Meanwhile, FIG. 5 illustrates the patient placement table 2 separated from the main body 3. The patient placement table 2 is made of a transparent synthetic resin and has a box shape (a box shape whose top surface is open) formed by disposing side plates 32*a*, 32*b*, 32*c*, and 32*d* with predetermined width upright near the front, rear, right, and left end edges of a rectangular bottom plate 31. The patient placement table 2 internally lays an elastic member made of polyurethane or a similar material. Band members 37, 37, and so on are symmetrically disposed by two at each of the front and the rear on the front side of the bottom plate 31. The band members 37, 37, and so on couple belts to secure (restrain) the patient at the required posture (a supine position, an abdominal position, or a similar position). The right and left side plates 32*a* and 32*b* have cutouts (notches) 33 with constant width at the front side parts. Furthermore, a plurality of taps 34, 34, and so on are disposed on the cutouts 33. With the taps 34, 34, and so on, arch-shaped shafts 35 and 35 can be mounted (threadably mounted) at any given front and rear positions. The arch-shaped shafts 35 and 35 function as mounting members to mount the securing means (securing units) 35*a*, which secure a chest of the patient. Additionally, rectangular engaging holes 36 and 36 are drilled near end edges at the front and the rear of the right and left side plates 32*a* and 32*b*. The engaging pieces 4, 4, and so on, which are on the top surface of the lower side beam 10, are insertable into the engaging holes 36 and 36.

<Method for Using Operating Table>

To perform the radiation therapy with proton beam on the patient P with breast cancer using the operating table 1 configured as described above, the patient P is placed on the bottom plate 31 (the elastic member) of the patient placement table 2. In this state, using the belts (not illustrated) attached to the band members 37, 37, and so on, the body of the patient P is secured at the required posture (the supine position). The patient placement table 2 on which the patient P is thus secured is inserted from the feet side of the patient P (or the head side of the patient P) from the front of the front side annular portion 7 to the inside so as to slide the top surface of the lower side beam 10. Thus, the patient placement table 2 is pushed in up to a position at which the end edge of the feet side of the patient P (or the head side of the patient P) projects to the rear of the rear side annular portion 8. Next, in this state, the engaging pieces 4, 4, and so on of the lower side beam 10 are engaged with the engaging holes 36 and 36 on the patient placement table 2, thus installing the patient placement table 2 to the main body 3. To push the patient placement table 2 inside, using the bearing members 26, 26, and so on of the lower side beam 10, the patient placement table 2 can be smoothly pushed. After the patient placement table 2 is thus mounted to the main body 3, a power source is supplied to the ball screws 18 and 18 and the pressing plate 17 is brought down up to an appropriate position at which the patient P can be loosely pushed.

After the patient placement table 2 and the main body 3 are coupled as described above, driving the motor 14 allows the patient placement table 2 to be rotated with respect to the main body 3 with the head-feet direction of the patient P as the rotation axis. That is, driving the motor 14 transmits the rotation force by the motor 14 to the front and the rear gears 24*a* and 24*b* via the shaft 25, thus rotating the gears 24*a* and 24*b*. The rotation of the gears 24*a* and 24*b* also rotates the inner ring-shaped gears, which mesh with the gears 24*a* and 24*b*, inside the front side annular portion 7 and the rear side annular portion 8. This rotates the patient placement table 2 pushed and secured between the upper side beam 9 and the lower side beam 10 with respect to the main body 3 with the head-feet direction of the patient P as the rotation axis. Stopping the supply of the electric power to the motor 14 secures the patient placement table 2 at a predetermined angle position. The controller incorporated into the drive control unit 5 controls the rotation angle of the motor 14 and the rotation angle of the patient placement table 2 with respect to the main body 3 is stored as necessary.

To perform the radiation therapy with proton beam on the patient P with breast cancer, in a state where the front and the rear inner ring-shaped gears are rotated by 180 degrees or any given angle such that the lower side beam 10 is positioned on the upper side, the patient P is secured with the securing means 35*a*, which are mounted to the arch-shaped shafts 35 and 35, with the breasts of the patient P drooped. After that, the patient placement table 2 is rotated again by 180 degrees or any given angle such that the lower side beam 10 is positioned on the lower side. In this state, the coupled state of the patient placement table 2 with the engaging pieces 4, 4, and so on is released. Only when the patient placement table 2 is separated from the main body 3 (Note that, in the operating table 1, when the lower side beam 10 is positioned at the lower side (when the top surface of the lower side beam 10 becomes horizontal), the coupled state of the patient placement table 2 with the engaging pieces 4, 4, and so on is configured to be released).

After the patient placement table 2 is separated from the main body 3 as described above, the patient placement table 2 is moved and loaded on a stretcher or a similar member for examinations required for the patient P such as MRI and CT (to identify the lesion site). After the examinations, the patient placement table 2 is moved and loaded on a bed for treatment with proton beam with the stretcher or a similar member as it is (with the posture and the breasts of the patient P secured on the patient placement table 2) for treatment with proton beam on the patient P. Thus performing the radiation therapy with proton beam on the patient P ensures utilizing results of the examinations (positional data of the lesion) and performing the radiation therapy with proton beam without giving negative effects on sites other than the lesion.

<Effects of Operating Table 1>

As described above, the operating table 1 includes the patient placement table (the patient placement securing means) 2, the main body 3, the engaging pieces (the coupling means) 4, 4, and so on, and the motor (the rotatable drive control means) 14. The patient placement table 2 is to place and secure the patient P in the required posture. The main body 3 supports the patient placement table 2. The engaging pieces 4, 4, and so on removably couple the patient placement table 2 to the main body 3. The motor 14 rotates the patient placement table 2 with the head-feet direction of the patient as the rotation axis to hold the patient placement table 2 at any given rotation angle. Accordingly, while the body of the patient P is secured (restrained) on the patient placement table 2 in the required posture, the patient placement table 2 can be separated from the main body 3. For example, before the radiation therapy with proton beam, the patient placement table 2 on which the patient P whose body is secured is placed is conveyed with the stretcher or a similar member for predetermined examinations on the patient P such as MRI and CT. After that, the patient placement table 2 is moved and loaded on the bed for treatment with proton beam as it is using the stretcher or a similar member. This makes the treatment with proton beam on the patient P who keeps the identical posture possible. Accordingly, with the operating table 1, the radiation therapy with proton beam can be effectively performed.

With the operating table 1, the patient placement table 2 includes the arch-shaped shafts 35 and 35, which are the mounting members, to mount the securing means 35a that secure a part of the body of the secured patient. For the radiation therapy with proton beam, the predetermined examinations and the radiation therapy with proton beam can be performed with the breasts of the patient P keeping away from the chest wall and secured and held with the securing means 35a on the patient placement table 2. Accordingly, with the operating table 1, the radiation therapy with proton beam can be more effectively performed.

Furthermore, the operating table 1 includes the bearing members (the movement and load assistance means) 26, 26, and so on, which use friction reduction members, on the surface (the top surface of the lower side beam 10) of the main body 3 in contact with the patient placement table 2. The use of the bearing member 26, 26, and so on allows the smooth separation of the patient placement table 2 from the main body 3 without applying a massive force. This also ensures moving and loading the patient placement table 2 from the stretcher or a similar member to the main body 3.

Additionally, with the operating table 1, the patient placement table 2 includes the strip-shaped side plates 32a and 32b with wide width disposed upright near both right and left end edges of the rectangular bottom plate 31. The cutouts 33 are disposed at a part of the side plates 32a and 32b. This ensures disposing the mounting members, which are to mount the securing means 35a to secure a part of the body, at positions appropriate for the patient and/or an affected part to be treated.

Even if the patient placement table 2 is rotated to be any posture, the operating table 1 holds the joined part at which the patient placement table 2 joins to the main body 3 without separation. Additionally, a deviation of the relative position between the patient placement table 2 and the main body 3 is held at required accuracy. Accordingly, the operating table 1 allows the patient P to have a sense of security. Additionally, the operating table 1 ensures the irradiation of proton beam on the lesion site at extremely good accuracy to treat the patient P with proton beam or a similar beam.

<Modification of Operating Table>

The configuration of the operating table according to the present invention is not limited to the aspects of the above-described embodiments, and configurations such as materials, shapes, structures of the patient placement securing means, the main body, the coupling means, the rotatable drive control means, the mounting member, the securing means, the movement and load assistance means, and similar means can be changed as necessary without departing from the spirit of the disclosure.

For example, the operating table is not limited to one that forms the cutouts on the side plates of the patient placement table like the above-described embodiment. The operating table can be changed to: one that forms cutouts on the bottom plate of the patient placement table, one that forms cutouts on both the side plates and the bottom plate, and one with a similar configuration. The operating table is not limited to one that includes the movement and load assistance means on the surface of the patient placement table in contact with the main body like the above-described embodiment. The operating table can be changed to: one that includes the movement and load assistance means on the surface of the main body in contact with the patient placement table, one that includes the movement and load assistance means on both surfaces of the patient placement table, and one with a similar configuration. Additionally, the movement and load assistance means using the friction reduction member is not limited to the bearing members like the above-described embodiment, the one that uses a wheel and one with a similar configuration may be used. Furthermore, the coupling means to couple the patient placement table to the main body is not limited to one that uses air pressure like the above-described embodiment. The coupling means can be changed to: one that uses a hydraulic pressure and one with a similar configuration. Additionally, the operating table is not limited to one that couples the sites near the four corners of the patient placement securing means to the main body with the coupling means like the above-described embodiment. The operating table can be changed to: one that couples the entire right and left side edges of the patient placement securing means to the main body, one that couples the entire outer peripheral edge of the patient placement securing means to the main body, and one with a similar configuration.

INDUSTRIAL APPLICABILITY

Since the operating table according to the present invention achieves excellent effects as described above, the operating table is applicable to examinations and treatments for various diseases. Especially, the operating table is preferably applicable as a device used for treatment with proton beam, treatment with heavy particle beam, and examinations for breast cancer.

DESCRIPTION OF REFERENCE SIGNS

1 . . . Operating table
2 . . . Patient placement table (patient placement securing means)
3 . . . Main body
4 . . . Engaging piece (coupling means)
13 . . . Bearing member (movement and load assistance means)
14 . . . Motor (rotatable drive control means)

The invention claimed is:
1. An operating table comprising:
a patient placement table that:
is rotatable about a head-feet direction as a rotation axis;
secures a patient placed in a supine position on a top of the patient placement table, also in a state where the patient placement table is rotated approximately 180 degrees; and
comprises an arch-shaped shaft for attaching a securing unit that secures a breast of the patient;

a main body that supports the patient placement table;

a coupling unit that removably couples the patient placement table to the main body; and a rotation mechanism that rotates the patient placement table about the rotation axis, while the patient placement table is coupled to the main body using the coupling unit, to hold the patient placement table at a predetermined rotation angle, wherein the securing unit secures and holds the breast of the patient when the rotation mechanism rotates the patient placement table approximately 180 degrees from the state that the patient is placed in the supine position on the top of the patient placement table.

2. The operating table according to claim 1, wherein while the patient placement table is rotated, the coupling unit holds a joined part at which the patient placement table and the main body are joined together without separation, and maintains positions of the patient placement table and the main body.

3. The operating table according to claim 1, further comprising:

the rotation mechanism further rotates the patient placement table approximately 180 degrees after the securing unit secures and holds the breast of the patient.

4. The operating table according to claim 1, wherein:

the patient placement table includes strip-shaped side plates disposed upright near both right and left end edges of a rectangular bottom plate, and at least one of the bottom plate and the side plates partially has a cutout.

5. The operating table according to claim 4, further comprising:

a plurality of taps that are disposed on the cutout and fix the arch-shaped shaft in a predetermined position in a longitudinal direction of the strip-shaped side plates.

* * * * *